United States Patent [19]

Strichartz et al.

[11] Patent Number: 5,288,723
[45] Date of Patent: Feb. 22, 1994

[54] A COMPOSITION AND A METHOD OF USING VERATRIDINE AND EPINEPHRINE AS A LOCAL ANESTHETIC

[75] Inventors: Gary R. Strichartz, Boston; Sanjay Datta, Newton Centre, both of Mass.; Markus Schneider, Basel, Switzerland

[73] Assignee: Brigham and Women's Hospital, Boston, Mass.

[21] Appl. No.: 779,197

[22] Filed: Oct. 22, 1991

Related U.S. Application Data

[63] Continuation-in-part of Ser. No. 754,915, Sep. 6, 1991, abandoned.

[51] Int. Cl.$^5$ .................. A61K 31/44; A61K 31/135; A61K 49/00
[52] U.S. Cl. .................. 514/279; 514/652; 514/653; 514/818; 424/10
[58] Field of Search .............. 514/169, 170, 652, 653, 514/171, 818, 279; 424/10

[56] References Cited

PUBLICATIONS

Chemical Abstracts (114: 199510s) 1991.
The Merck Index "Epinephrine 3543" 9th Ed. 1983.
Ganong, W. F., Review of Medical Physiology, 9th ed., Chapter 2, pp. 29–34, Lange Medical Pub., Los Altos, Calif. (1979).
Windholz, M., et al. (eds), The Merck Index, (10th ed), p. 1422, Merck & Co., Inc., Rahway, N.J. (1983).
Goodman and Gilman (eds), The Pharmacological Basis of Therapeutics, 8th ed., Chapter 15, pp. 311–331, Pergamon Press, N.Y. (1990).
Schneider, M., et al., Anesthesiology 73:3A:A790 (1990).
Schneider, M., et al., Anesthesiology 74:270–280 (1991).
Strichartz, G. R., et al., Anesthesiology 75:3A:A771 (1991).
Hunt, et al., In Vitro and In Vivo Action of Veratridine on the Rat Sciatic Nerve, poster presentation at Oct. 29, 1991 Annual Meeting of the American Society of Anesthesiologists, San Francisco, Calif.

*Primary Examiner*—Frederick E. Waddell
*Assistant Examiner*—K. Weddington
*Attorney, Agent, or Firm*—Sterne, Kessler, Goldstein & Fox

[57] ABSTRACT

A method of using veratridine to inhibit nerve impulses, and a composition of matter including veratridine and epinephrine, is provided. Application of veratridine proximal to a nerve causes depolarization of the nerve membrane, thereby blocking transmission of nerve impules. C-fiber selectivity is demonstrated in vitro in rabbit vagus nerves. Veratridine displays extended anesthetic activity over long periods of time when compared to similar local anesthetics, with no local toxicity. Systemic toxicity is reduced by co-injection with epinephrine.

6 Claims, 8 Drawing Sheets

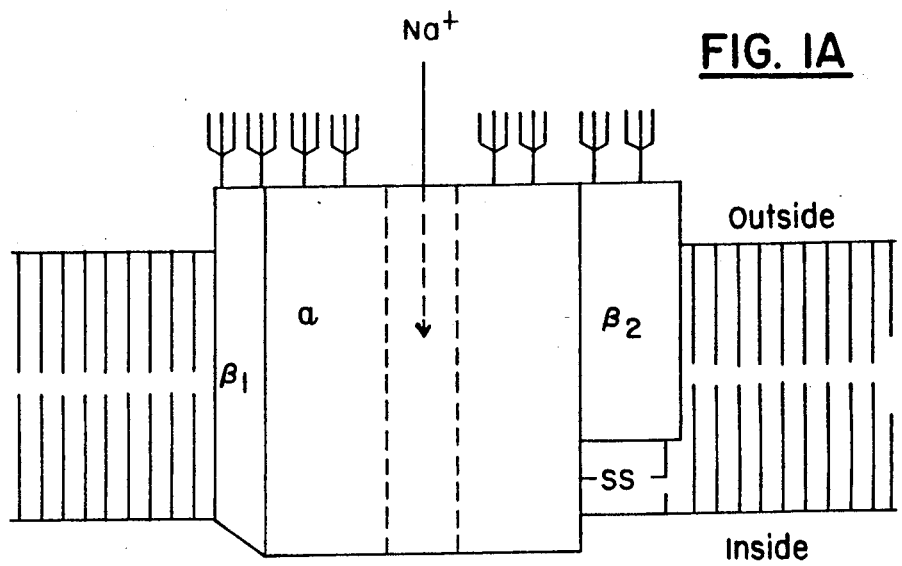
FIG. IA
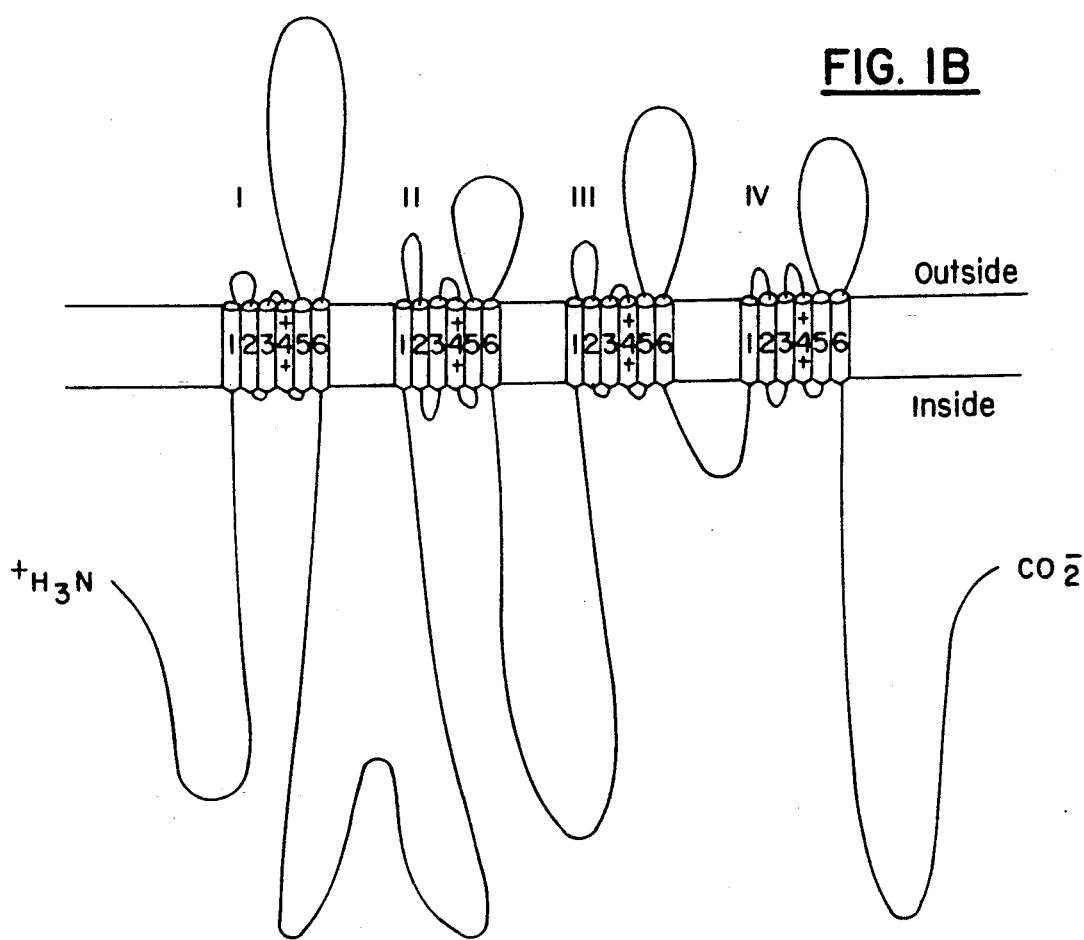
FIG. IB

EXTRACELLULAR RECORDING CHAMBER

SUCROSE-GAP CHAMBER

| CONTROL | VTD | WASH |
|---|---|---|
| 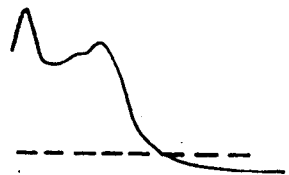 | 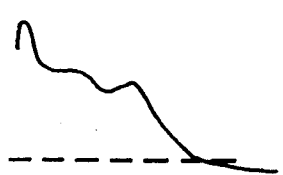 | 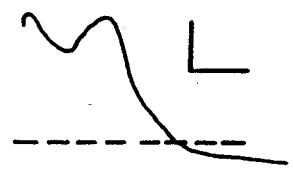 |
| FIG. 3A | FIG. 3B | FIG. 3C |
| 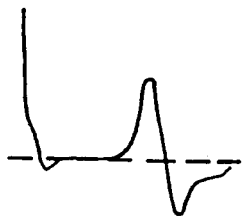 |  | 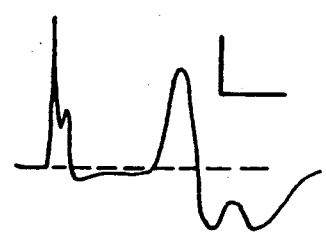 |
| FIG. 3D | FIG. 3E | FIG. 3F |
| CONTROL | VTD | WASH |
|---|---|---|
|  |  |  |
| FIG. 6A | FIG. 6B | FIG. 6C |

CONTROL
FIG. 5A
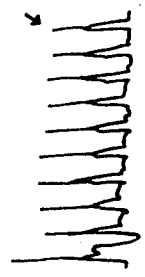
FIG. 5D
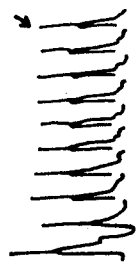
FIG. 5G
VTD
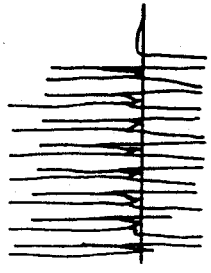
FIG. 5B
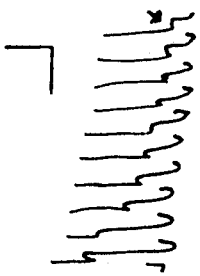
FIG. 5E
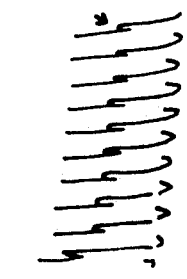
FIG. 5H
WASH
FIG. 5C
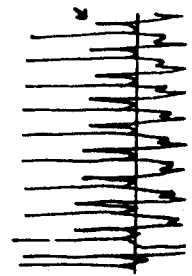
FIG. 5F
FIG. 5I CONTROL 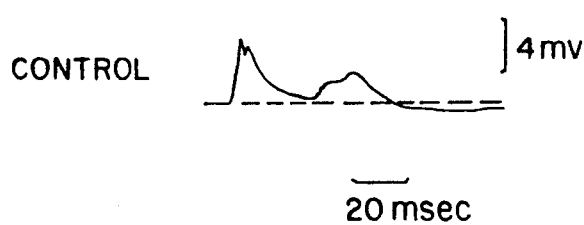 ]4mv
~20 msec
FIG. 8A
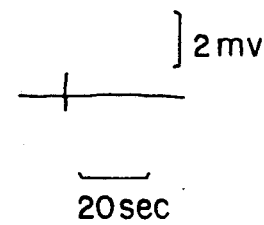 ]2mv
~20 sec
FIG. 8B
VTD 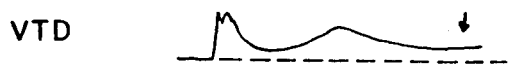
FIG. 8C
FIG. 8D
CONTROL 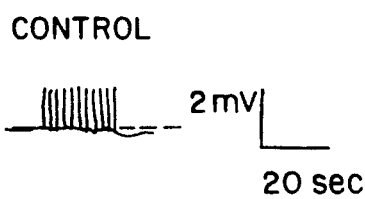 2mV
20 sec
FIG. 9A
VTD 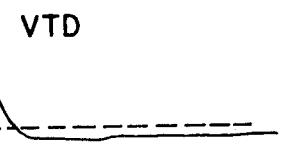
FIG. 9B
VTD 4mV
20msec
FIG. 9C
VTD
FIG. 9D

A COMPOSITION AND A METHOD OF USING VERATRIDINE AND EPINEPHRINE AS A LOCAL ANESTHETIC

This invention was made with United States Government support, and the Government has certain rights in this invention.

CROSS-REFERENCE TO RELATED APPLICATIONS

The present application is a continuation-in-part of U.S. patent application Ser. No. 07/754,915, filed Sep. 6, 1991, now abandoned, the contents of which are fully incorporated herein by reference.

FIELD OF THE INVENTION

The present invention relates generally to methods for producing a local anesthetic effect. More particularly, this invention relates to a method for producing a local anesthetic effect by placing in proximal contact with a nerve an effective amount of the compound veratridine.

BACKGROUND OF THE INVENTION

Local anesthetics are drugs that block nerve conduction when applied locally to nerve tissue in appropriate concentrations. Generally, they act on any part of the nervous system and on every type of nerve fiber. Thus, a local anesthetic in contact with a nerve trunk can cause both sensory and motor paralysis in the area innervated. A preferred practical characteristic of compounds that are termed local anesthetics is that their action is reversible; i.e., that their use is followed by complete recovery of nerve function with no evidence of structural damage to nerve fibers or cells.

A suitable local anesthetic should combine several properties. It should not be irritating to the tissues to which it is applied, nor should it cause any permanent damage to nerve structure. Its systemic toxicity should be low because it is eventually absorbed from its site of application. The ideal local anesthetic must be effective regardless of whether it is injected into a tissue or applied locally to mucous membranes. It is usually important that the time required for the onset of anesthesia should be as short as possible. Furthermore, the action must last long enough to allow time for the contemplated surgery, yet not so long as to entail an extended period of recovery. Occasionally, a local anesthetic action lasting for days or even weeks or months is desirable, for example, in the control of chronic pain. Unfortunately, the available compounds employed for anesthesia for such long duration have high local toxicity. Neurolysis with slough and necrosis of surrounding tissues occur, and partial or complete transverse injury of the spinal cord with permanent paralysis may result if such a reaction occurs in the vicinity of the cord.

Local anesthetics prevent the generation and the conduction of the nerve impulse. Their main site of action is the cell membrane, since conduction block can be demonstrated in giant axons from which the axoplasm has been removed.

Local anesthetics block conduction by decreasing or preventing the enlarged transient increase in the permeability of excitable membranes to $Na^+$ that is produced by a slight depolarization of the membrane (see Strichartz, G. R., and Ritchie, J. M., "The action of local anesthetics on ion channels of excitable tissues," in *Local Anesthetics* (Strichartz, G. R., ed.), *Handbook of Experimental Pharmacology*, Vol. 81, Springer-Verlag, Berlin, pp. 21–53 (1987)). This action of local anesthetics is due to their direct interaction with voltage-sensitive $Na^+$ channels. As the anesthetic action progressively develops in a nerve, the threshold for electrical excitability gradually increases, the rate of rise of the action potential declines, impulse conduction slows, and the safety factor for conduction decreases. These factors decrease the probability of propagation of the action potential, and nerve conduction fails.

Although a variety of physicochemical models have been progosed to explain how local anesthetics achieve conduction block (see Courtney, K. R., and Strichartz, G. R., "Structural elements which determine local anesthetic activity," *Id.*, pp. 53–94), it is now generally accepted that the major mechanism of action of these drugs involves their interaction with a specific binding site within the $Na^+$ channel. However, whether or not all actions of local anesthetics are mediated by a common site remains unclear (Courtney and Strichartz, supra; Strichartz and Ritchie, supra).

Biochemical, biophysical, and molecular biological investigations during the past decade have led to a rapid expansion of knowledge about the $Na^+$ channel and other voltage-sensitive ion channels (see Catterall, W. A., "Structure and function of voltage-sensitive ion channels," *Science* 242:50–61 (1988); Trimmer, J. S., and Agnew, W. S., "Molecular diversity of voltage-sensitive Na channels," *Annu. Rev. Physiol.* 51:401–418 (1989)). The $Na^+$ channel of the mammalian brain is a heterotrimeric complex of glycosylated proteins with an aggregate molecular size in excess of 300,000 daltons; the individual subunits are designated $\alpha$ (260 kilodaltons), $\beta_1$ (36 kilodaltons), and $\beta_2$ (33 kilodaltons). After incorporation of the purified polypeptides into phospholipid vesicles, sodium flux into these vesicles occurs in response to veratridine, a substance known to cause persistent activation of $Na^+$ channels. Only the $\alpha$ subunit is required to reconstitute channel function. Movement of $Na^+$ into the vesicles is blocked by the neurotoxins tetrodotoxin and saxitoxin, and by local anesthetics (Tamkun et al., "The sodium channel from rat brain; reconstitution of neurotoxinactivated ion flux and scorpion toxin binding from purified components," *J. Biol. Chem.* 259:1676–1688 (1984)). The hydrophilic neurotoxins probably bind within the mouth of the channel which is formed by the $\alpha$ subunit. By use of a nonpermeant quaternary analog of lidocaine, it is possible to show that local anesthetics and tetrodotoxin interact at opposite ends of the $Na^+$ channel (Rosenberg et al., "Reconstitution of neurotoxin-modulated ion transport by the voltage-regulated sodium channel isolated from the electroplax of *Electrophorus electricus*," *Proc. Natl. Acad. Sci. USA* 81:1239–1243 (1984)). A simple model of the $Na^+$ channel in the plasma membrane is shown in FIG. 1.

It is well known that different nerve fiber types have varying relative susceptibilities to conduction block produced by local anesthetics. The various fiber types are generally classifiable into type A, type B, and type C. Generally, the greater the diameter of a given nerve fiber, the greater its speed of conduction. The larger axons are concerned with proprioceptive sensation and somatic motor function, while the smaller axons subserve temperature and pain sensation and autonomic function. In Table 1, the various fiber types are listed with their diameters, electrical characteristics, and functions.

TABLE 1
Nerve Fiber Types in Mammalian Nerve

| Fiber Type | | Function | Fiber Diameter (μm) | Conduction Velocity (ms) | Spike Duration (ms) | Absolute Refractory Period (ms) |
|---|---|---|---|---|---|---|
| A | α | Proprioception; somatic motor | 12–20 | 70–120 | 0.4–0.5 | 0.4–1 |
|   | β | Touch, pressure | 5–12 | 30–70 | | |
|   | γ | Motor to muscle spindles | 3–6 | 15–30 | | |
|   | δ | Pain, temperature, touch | 2–5 | 12–30 | | |
| B |   | Preganglionic autonomic | <3 | 3–15 | 1.2 | 1.2 |
| C | dorsal root | Pain, reflex responses | 0.4–1.2 | 0.5–2 | 2 | 2 |
|   | sympathetic | Postganglionic sympathetics | 0.3–1.3 | 0.7–2.3 | 2 | 2 |

In addition to variations in the speed of conduction and fiber diameter, the various classes of fibers in peripheral nerves differ in their sensitivity to hypoxia (Table 2). This fact has clinical as well as physiologic significance. Pressure on a nerve can cause loss of conduction in motor, touch, and pressure fibers while pain sensation remains relatively intact.

TABLE 2
Relative Susceptibility of Mammalian A, B, and C Nerve Fibers to Conduction Block Produced By Various Agents

| | Most Susceptible | Intermediate | Least Susceptible |
|---|---|---|---|
| Sensitivity to hypoxia | B | A | C |
| Sensitivity to pressure | A | B | C |

The differential rate of block exhibited by fibers of varying sizes is of great practical importance and may explain why local anesthetics affect the sensory functions of a nerve in a predictable order. Fortunately for the patient, the sensation of pain is usually the first modality to disappear; it is followed in turn by the sensations of cold, warmth, touch, and deep pressure, although individual variation is great.

The degree of block produced by a given concentration of local anesthetic depends markedly on how much and how recently the nerve has been stimulated. Thus, a resting nerve is much less sensitive to a local anesthetic than one that has been recently and repetitively stimulated; the higher the frequency of preceding stimulation, the greater is the degree of block obtained to a test shock. These frequency and use dependent effects of local anesthetics seemingly occur because the local anesthetic molecule in its protonated or charged form gains access to its binding site only when the $Na^+$ channel is in an open state and because the local anesthetic may bind more tightly to and stabilize the inactivated state of the $Na^+$ channel (see Courtney and Strichartz, supra). Measurements of single channel events show that voltage dependent activation is immediately followed by formation of an inactivated state. It is this transition that closes the channel (Aldrich et al., "A reinterpretation of mammalian sodium channel gating based on single channel recording," *Nature* 306:436–441 (1983)). Once bound, the local anesthetic greatly restricts the conformational changes in the sodium channel that underlie activation (Butterworth, J. F., and Strichartz, G. R., "Molecular mechanisms of local anesthesia: a review," *Anesthesiology* (1990, in press).

Veratridine is a classic activator of the voltage-gated $Na^+$ channel. Veratridine binds to and selectively stabilizes an open conformation of the $Na^+$ channel, leading to a persistent increase in $Na^+$ permeability and a concomitant membrane depolarization. Veratridine binding and the associated depolarization are antagonized competitively by local anesthetics, and in principle, local anesthetic binding should be antagonized by veratridine.

Veratridine is a member of the veratrum alkaloids. The veratrum alkaloids constitute an abundant group of steroid-like polycyclic nitrogen-containing ring structures found in liliaceous plants. The alkaloids in two veratrum species, *Veratrum album*, Linn, and *Veratrum viride*, Aiton, and the species *Schoenocaulon officinale*, Gray, have been perhaps the best characterized, although as many as 20 different alkaloids have been identified to date (Krayer, O., and Acheson, G. M., *Physiol. Rev.* 26:336–446 (1946); Krayer, O., "Veratrum Alkaloids" in *Pharmacology in Medicine*, V. A. Drill (ed.), McGraw-Hill, N.Y. (1958)).

Veratridine, one of the major alkaloid components of veratrine, which is extracted from the seeds of Schoenocaulon officinale, the "Sabadilla seeds," has been widely used as a neuropharmacological tool to study the electrical properties of nerve and muscle fibers. Ulbricht, W., *Rev. Physiol.* 61:18–71 (1969); Ohta, M., et al., *J. Pharmacol. Exp. Ther.* 184:143–154 (1973); Catterall, W. A., *Ann. Rev. Pharmacol. Toxicol.* 20:15–43 (1980). Its ability to depolarize cells by altering the membrane-associated sodium channels is now well documented. Ulbricht, supra.

Aside from the well known use of veratridine as a sodium channel activator, veratridine has also been investigated as a potential hypotensive agent. Aviado, Domingo M., *Pharmalogic Principles of Medical Practice*, Williams & Wilkins, Baltimore, p. 548 (1972). Veratridine has also been reported as a selective inhibitor of angiotensin II receptors. Ball, D., et al., "Veratridine, Angiotensin Receptors and Aldosteronogenesis in Bovine Adrenal Glomerulosa Cells," *Clin. and Exper. Theory and Practice* A8(3):323–345 (1986).

SUMMARY OF THE INVENTION

In seeking a means to reverse local anesthetic block of peripheral nerve, the actions of veratridine (VTD) were examined, an agent known to competitively antagonize the binding of local anesthetics to sodium channels. The actions of VTD, a steroidal alkaloid "activator" of voltage-gated sodium channels, were studied in the rabbit vagus nerve by two methods. In one, the effects of VTD on compound action potentials ($AP_c$) propagating through a "veratrinized" segment (11-mm) of nerve were measured by extracellular recording. Single volleys of impulses were unaffected by VTD, but trains of impulses, triggered by repetitive stimulation, were selectively diminished. This "use-dependent" reduction was greatest for the C-fiber component of the $AP_c$, less for B-fibers, and inconsequential for A-fibers. Use-dependent inhibition was enhanced by higher stimulation frequency and by increased VTD concentration, and reversed rapidly when stimulation ceased. If the nerve sheath remained intact, the rate of VTD action was far less than in desheathed nerves, but the effects were the same.

In a second experimental system, membrane potentials were measured in the veratrinized region of the nerve by the "sucrose-gap" method. Repetitive stimulation, particularly of C-fibers, produced a cumulative VTD-induced depolarization (VID) that was sustained over several seconds and during which the C-fiber $AP_c$ was selectively reduced. We propose that this local, use-dependent VID provides the means to inhibit impulses propagating through the veratrinized region. The preferential effect of VTD on C-fibers suggests its possibilities as a relatively selective agent for block of impulse trains in nociceptive (pain) afferents.

The degree and duration of block was also studied in follow-up in vivo studies that demonstrated the enhanced activity of VTD as a local nerve blocker of rat sciatic nerve. VTD alone, and VTD in combination with epinephrine (EPI), were compared to the common local anesthetics bupivacaine and lidocaine. EPI decreases the toxicity associated with higher concentrations of VTD. We concluded that VTD is a more potent and longer-acting inhibitor of motor function than either bupivacaine or lidocaine, although nocifensive reflexes are blocked less predictably.

The present invention is directed to a method for inhibiting nerve impulses, comprising administering a therapeutically effective amount of veratridine or a pharmaceutically acceptable salt thereof proximal to at least one nerve, in an animal (including a human). Veratridine is represented by the following structural formula:

The method involves application of VTD to motor and/or sensory nerves containing A-fibers, B-fibers, and C-fibers.

Also disclosed is a method and composition for inhibiting nerve impulses wherein VTD is co-injected with an amount of epinephrine effective to reduce toxicity in an animal or human.

An advantage of the present invention is the C-fiber selectivity demonstrated in in vitro studies of the local anesthetic activity of VTD on rabbit vagus nerves. The demonstrated selectivity for block of the nerve fiber type that is most commonly associated with the transmission of pain signals is a marked departure from previously known anesthetics.

Another advantage of the present invention is the enhanced duration of the nerve block demonstrated in in vivo studies of rat sciatic nerve by VTD. Compared to bupivacaine and lidocaine, veratridine demonstrates longer duration than both. Co-administration with epinephrine reduces the systemic toxicity associated with veratridine.

BRIEF DESCRIPTION OF THE DRAWINGS

FIG. 1A is a model of the voltage-sensitive sodium channel from mammalian brain in the plasma membrane. The $\alpha$ and $\beta_1$ subunits interact noncovalently; the $\alpha$ and $\beta_2$ subunits are linked by disulfide bonds. The branched structures at the outer surface of the channel represent oligosaccharides.

FIG. 1B is a proposed transmembrane arrangement of the $\alpha$ subunit of the sodium channel. Four homologous domains (I-IV) each consist of six stretches of hydrophobic amino acid residues that are thought to cross the plasma membrane. The S4 segment contains positively charged residues. (Modified from Catterall et al., 1988).

FIGS. 3A-F are oscilloscopic recordings of $AP_c$s stimulated by single shocks for A- and B-fibers (A-C), and for C-fibers (D-F). The control records (A,D) were taken 5-7 min. before exposure to VTD (2uM). VTD records (B,E) were taken after 15-20 min. exposure to drug, and wash records (C,F) were taken 20-30 mins. after switching to drug-free perfusate. Calibration scale: vertical, 0.8 mV; horizontal, 4 ms (A-C), and 20 ms (D-F). The broken lines represent the zero potential baselines.

FIG. 5 depicts oscilloscopic traces of examples of use-dependent actions of VTD on A-fibers (A-C), B-fibers (D-F), and C-fibers (G-I). Trains of ten action potentials were stimulated by the appropriate stimuli (see Conditions for Examples 1-3), and the corresponding action potentials (shown by the arrows for the last $AP_c$ in control and VTD panels) were followed at different frequencies and conditions. For A-fibers, [VTD]=2 µM and $f_{stim}$=100 Hz; calibrations are 0.8 mV and 20 ms. For B-fibers [VTD]=2 µM and $f_{stim}$=50 Hz; calibrations are 0.8 mV and 40 ms. For C-fibers [VTD]=0.2 µM and $f_{stim}$=10 Hz; calibrations are 0.4 mV and 0.2 s.

FIGS. 6A-C show superimposed oscilloscopic traces showing use-dependent inhibition and slowing of C-fiber $AP_c$ by VTD (2 µM). (A) Control records 10 min. before VTD at 2-Hz stimulation frequency show almost complete overlap of traces 1-10. (B) During VTD exposure (15-20 min.), the second through tenth $AP_c$s in the train show a slowed conduction and reduced amplitude (5-Hz stimulation frequency). (C) After 20 min. in VTD-free HL (wash) the use-dependent effects measured at 5 Hz have largely reversed.

FIGS. 8A-D show sucrose-gap recordings of compound action potentials in the veratrinized region of nerve. Fast oscilloscope traces (A, C) show the $AP_c$ and the beginning of the veratridine-induced depolarization (VID: arrow, C). Slow strip-chart records show the time course of the VID resulting from a single stimulus (D) and its absence without VTD (B). VTD=2.0 µM. (Fast action potentials are not faithfully recorded in the strip-chart measurements, but the VID is followed precisely.) The broken line marks the baseline for zero change in membrane potential.

FIG. 9 shows sucrose-gap recordings of VTD effects during repetitive stimulation. Strip-chart recordings of responses to 0.5 Hz stimulation in control (A) and VTD-containing (0.2 µM) perfusate (B) show the cumulative VID during repetitive stimulation. The $AP_c$s during this VID are shown for the first stimulus (C) and the tenth stimulus (D) in the train. The deflection arising from C-fiber activity, shown by the double-ended arrows, is reduced by 40% between the beginning and end of the train, whereas that from A-fibers is unchanged.

DETAILED DESCRIPTION OF THE PREFERRED EMBODIMENT

Figure 2A:
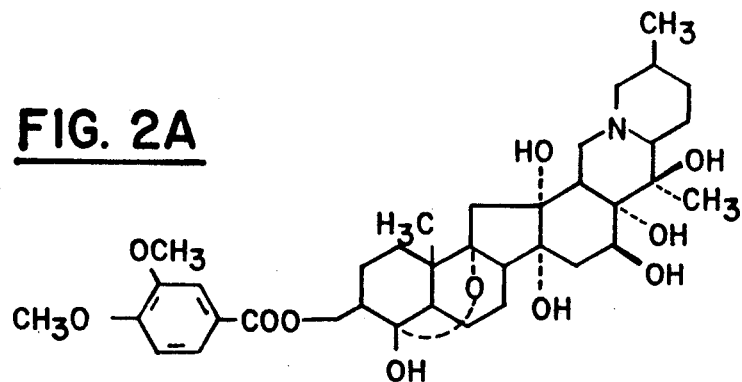
FIG. 2A is a structural formula of the chemical veratridine.

The invention relates to a method for inhibiting the conduction of nerve impulses, along a nerve comprising administering a therapeutically effective amount of veratridine (VTD) or a pharmaceutically acceptable salt thereof, proximal to said nerve, to an animal or human being.

VTD binds to and selectively stabilizes an open conformation of the voltage dependent sodium channel, leading to a persistent increase in sodium permeability and a concomitant nerve membrane depolarization. Surprizingly, the addition of VTD to a nerve during recovery from the local anesthetic bupivacaine potentiated rather than antagonized the residual block. Furthermore, VTD alone resulted in impulse inhibition that was highly preferential for C-fibers, in a "use-dependent" manner. The in vitro selective effects of VTD on the compound action potential ($AP_C$) of a mammalian peripheral nerve are demonstrated here for the first time. The results demonstrate the dependence of inhibition on impulse frequency over a range of drug concentrations in the $AP_C$ elevations of A-, B- and C-fibers. It also reports the action of VTD on impulses in a nerve with an intact sheath: since the sheath is somewhat permeable to the drug, the drug is shown to be a potentially useful local anesthetic. Also demonstrated, by the sucrose-gap method of examination of the compound (average) resting potential of the nerve, is that local depolarization of the nerve in the region exposed to VTD provides the mechanism for this selective inhibition. In vivo effects are demonstrated in rat sciatic nerve wherein VTD is administered alone, and with epinephrine.

The term "inhibiting nerve impules" means in the context of the present invention to decrease the amplitude and/or frequency of a propagated nerve-fiber action potential ($AP_c$). The meaning of the term "action potential" is well-known to those of ordinary skill in the art to describe the physiological phenomenon whereby an electrical disturbance or signal is propagated along the length of a nerve membrane. A "nerve impulse" is an action potential propagated along a nerve fiber. A "nerve" is construed to mean a bundle of nerve fibers of varying types and functions, covered by a sheath.

The term "thereapeutically effective amount" means in the context of the present invention an amount of veratridine effective to measurably decrease the amplitude and/or frequency of nerve impulses. The present invention provides methods of measuring this inhibition in vitro, and in vivo. Clinically, the term means that amount of veratridine that will cause a noticeable reduction in motor, nociceptive, or proprioceptive sensory reception. Therapeutically effective amounts can be delivered in any number of ways, including surface (topical) anesthesia, infiltration anesthesia for minor surgery, field block anesthesia, and nerve block anesthesia. This list is not intended to be complete, but merely illustrative of those techniques that are known to those of ordinary skill in the anesthesia art. Typical "therapeutically effective amounts" include 0.027 to 0.63 mg/kg of body weight, more preferably, 0.027 to 0.27 mg/kg of body weight.

"Veratridine" (VTD) is an alkaloid neurotoxin which depolarizes tissues that incorporate the voltage-dependent sodium channel. It is a natural product derived from the mixture of compounds called veratrine, which is in turn derived from the seeds of *Schoenocaulon officinale*. VTD and its prior art uses are more fully described in the Background section. A monograph on VTD can be found in The Merck Index, 11th ed., (1989) under Reference No. 9855.

In the present invention the term "proximal to at least one nerve" means close enough to a minimum of one nerve for VTD to penetrate the ensheating tissue and come into physical contact with the fibers within it. This includes injection into tissue local to the nerve, followed by diffusion of the VTD-containing solution into direct contact with the nerve. Also contemplated is the injection or placement of extended-release formulations of VTD, including microsphere carriers or lipid-based emulsions, into close contact with the nerve. Direct contact is not necessary, if diffusion of VTD into direct contact with the nerve occurs. Formulations of VTD that enable diffusion through the skin, such as in combination with Dimethyl sulfoxide (DMSO), also come within the scope of the invention.

The present invention contemplates the efficacy of VTD on the three major types of nerve fibers. A-, B- and C-fibers are all affected, though differently, by VTD. As more fully described in the Background section, nerve fibers are affected differentially by anesthetics.

The invention of the present application contemplates the co-administration of VTD with epinephrine (EPI), when necessary to negate systemic toxicity. EPI has demonstrated ability to decrease VTD-associated toxicity (see Example 6). Also, EPI has known effectiveness in increasing the duration of local anesthetics. It is contemplated that pharmaceutically acceptable formulations of VTD may include EPI or other agents with similar toxicity-mitigating qualities, known to those of ordinary skill in the art. The ratio of EPI to VTD that may be effective is on the order of approximately 1:200,000.

Also included within the scope of the present invention are the non-toxic pharmaceutically acceptable salts of the compounds of the invention. Nitrates and sulfates in particular are included, but any salt capable of forming an adduct with an alkaloid is considered within the scope of this invention.

Suitable formulations for parenteral administration include aqueous solutions of veratridine in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Topical formulations are also contemplated, in particular for surface anesthesia.

The following examples are illustrative, but not limiting, of the method and compositions of the present invention. Other suitable modifications and adaptations of the invention as well as the variety of conditions and parameters normally encountered in clinical therapy and which are obvious to those skilled in the art are within the spirit and scope of the invention.

CONDITIONS FOR EXAMPLES 1-3

Animals used in this study were maintained and treated in accordance with the guidelines of the Committee on Animals of the Harvard Medical School.

Adult male New Zealand white rabbits (3±0.5 kg) were pretreated intramuscularly with a mixture of ketamine (200 mg), xylazine (20 mg) and atropine (0.4 mg) for sedation. Ten minutes after this treatment, the animals were anesthetized with diethyl ether. After cessation of respiration, a longitudinal skin incision was made, and the cervical portion of both vagus nerves was dissected. The vagus nerves were temporarily stored at room temperature (22° C.) in a beaker containing modified HEPES Liley (HL) solution stirred constantly by aeration with a mixture of 95% oxygen and 5% carbon dioxide.

The modified HL solution used for bathing the nerve and subsequent drug perfusion consisted of (in mM): NaCl, 118.0; KCl, 5.0; $CaCl_2 2H_2O$, 2.0; $MgCl_2 6H_2O$, 1.0; α-D(+)-glucose, 11.0; $NaHCO_3$, 25.0; and N-2-hydroxy-ethylpiperazine-N-2-ethanesulfonic acid (HEPES) buffer, 5.0 mM. The pH was adjusted to 7.4±0.05 by addition of 1 N NaOH. The perfusion solution was bubbled with a gas mixture of 95% oxygen and 5% carbon dioxide at a vigorous rate just before flowing onto the nerve. The pH was stabilized by the HEPES buffer and maintained at 7.4.

VTD free base (no. V-5754, lot 58F-7828, Sigma, St. Louis, Mo.) was stored in a desiccator below 0° C. and was used to prepare a 2 mM stock solution in dimethyl sulfoxide [DMSO], Fisher Scientific, lot 861316), which also was stored at below 0° C. VTD, a steroidal alkaloid (FIG. 2A) that is produced by certain lilies, has a solubility limited to approximately $10^{-3}$ M in aqueous slat solutions [Kupchan and By, "The Veratrum Group," in Alkaloids, Vol. 10, Manske, R.H.F. (ed.), New York, Academic Press (1968), pp. 193-285]. The stock VTD solution was diluted to final concentrations of 0.2-10 μM by the addition of HL. The maximum equivalent content of DMSO is 0.5%, and in three control experiments we detected no change in electrophysiologic behavior with 1% DMSO.

EXAMPLE 1

Extracellular Recording

The nerves were cleaned and desheathed by microdissection before mounting in an airtight chamber (FIG. 2B) [Gissen et al., *Anesthesiology* 53:467-474 (1980)]. Petroleum jelly (White Petrolatum, Denison Laboratories) seals separated a central, 11-mm length of the nerve from the lateral pools, used for stimulating and recording with electrodes made of platinum wire. The central section of the chamber (volume 0.25 ml) was perfused with HL solution at 0.5 ml.min.$^{-1}$. The lateral pools containing the moistened ends of the nerves adsorbed to the electrodes were filled with paraffin oil. The $AP_c$s were propagated over 21 mm, from the stimulating to the recording electrodes, with the proximal recording electrode located 4.5 mm from the edge of the central, drug exposure chamber. Thus, measured $AP_c$s were conducted in nerve exposed to drug for half of the conduction pathway, and had been conducting through drug-free medium over a distance containing at least two or three nodes of Ranvier (in the fastest-conducting fibers), before reaching the recording electrodes.

The stimulus intensities and durations, supplied by Grass S-88 stimulators (Grass Instrument, Braintree, Mass.), were adjusted to produce the appropriate maximum $AP_c$ as displayed on storage oscilloscopes (3–12 V for 0.05 ms, for A-fibers; 6–14 for 0.1 ms, for B-fibers; and 8–24 V for 1.0 ms, for C-fibers) (model 5113, Tektronix, Beaverton, Oreg.). The signal from the nerve was amplified 50 times (model AK 475 operational amplifier, Metametrics, Carlisle, Mass.) and passed to the oscilloscope preamplifiers (model 5A 22N, Tektronix). The preparation was not considered acceptable unless the $AP_c$ signals from the nerve exceeded 1.5 mV for A-fibers, 0.5 mV for B-fibers, and 0.3 mV for C-fibers.

Figure 2B:
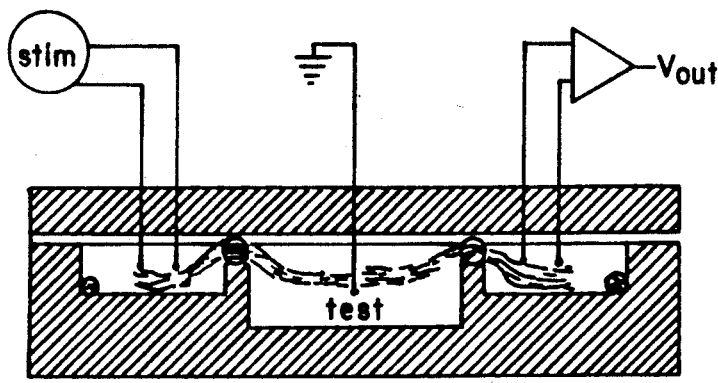
FIG. 2B is a cross-sectional view of the extracellular recording chamber, showing the lateral stimulating and recording chambers, and the central grounded "test" pool through which VTD was perfused. Petroleum jelly seals are shown by cross-hatching.

Each nerve was exposed to only one VTD concentration, and each concentration was tested in four or five separate nerves, except in tie sheathed nerves, for which only two nerves were used. The temperature was 20°–22° C. $AP_c$s stimulated by single shocks are shown in FIG. 2.

EXAMPLE 2

Control Recording

In a series of control experiments, nerves were continuously perfused with only HL solution for a total period of 60 min. (four nerves) or 175 min. (one nerve). After 60 min, in the control solution, a time corresponding to a 35-min. exposure to VTD (see FIG. 4, top), the different $AP_c$ components had the following values relative to the amplitudes at 25 min. ("zero" time in FIG. 4): A-fibers, 118±13%., n=4; B-fibers, 126±19%, n=4; C-fibers, 96.5±7.9%, n=4. In the one control nerve continuously exposed to HL for 175 min., the $AP_c$ amplitudes at the end, corresponding to 75 min. of HL wash after 75 min. exposure to VTD (see FIG. 4), were the following percentages of the 25-min. values: A-fibers, 147%; B-fibers, 148%; and C-fibers, 153%. These single measurements are slightly higher than the average values recorded at the end of the wash-out after VTD exposure (FIG. 4 top).

EXAMPLE 3

Sucrose-Gap Recording

Figure 2C:
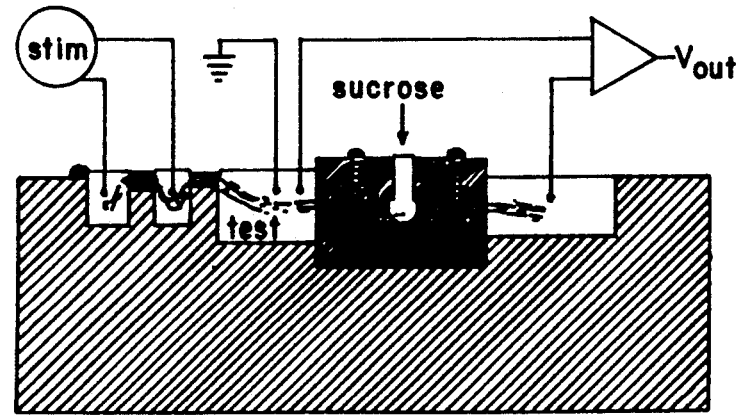
FIG. 2C is a cross-sectional view of the sucrose-gap chamber, showing the separate stimulus pools, the "test" pool for drug perfusion, and the "distal" pool containing the cut end of the nerve bathed in HEPES-Liley solution. A central gap of 3 mm provided a conduit for the continuous perfusion of an intermediate segment of the nerve by isotonic sucrose.
Figure 4A:
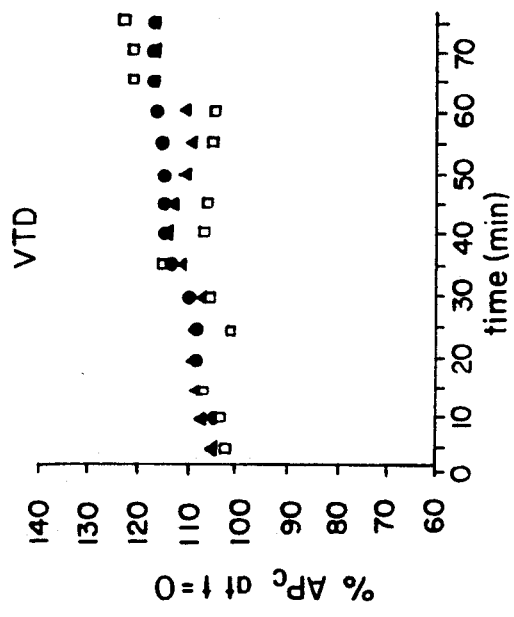
FIG. 4 shows the average change caused by VTD (0.5 µM) in the height of singly stimulated compound action potentials (4A-C) and in the ratio of the height of the tenth to the height of the first action potential in a train (4D-F). Amplitudes for A- (circles), B- (squares), and C-fibers (triangles) in the top 3 panels are expressed relative to the amplitude at t=0, the beginning of VTD perfusion, shown by the asterisk in the control panel. Times before that are negative. The use-dependent reduction of the $AP_c$ amplitude (4D-E) is graphed as the average ratio in peak heights between the last and first action potential in a train of ten (see examples in FIG. 5). Each fiber type was tested, and its appropriate stimulus condition (see Conditions for Examples 1-3, below) delivered at the frequency noted on the horizontal scales of 4D-4F. These tests occurred at the experimental time axes in the top panels (e.g., 4A relevant for 4C; 4B for 4E, etc.). During the control period only one cycle of stimulation frequencies (0.1-100 Hz) was applied (FIG. 4D). Two cycles were applied during the VTD and wash periods (4E, 4F), the first occurring from 0-30 min. and ranging in frequency from 0.1 to 10 Hz, and the second beginning at 30 min. and extending to 100 Hz. All are averages from three to four separate nerves.
Figure 4B:
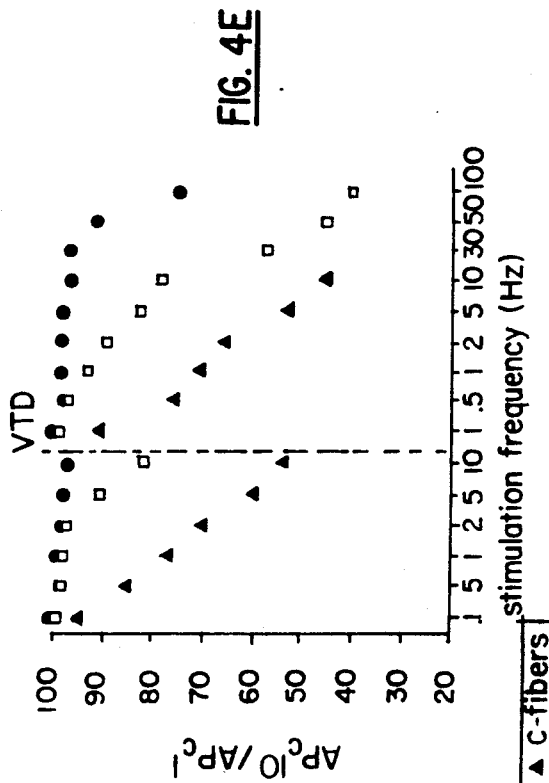
Figure 4D:
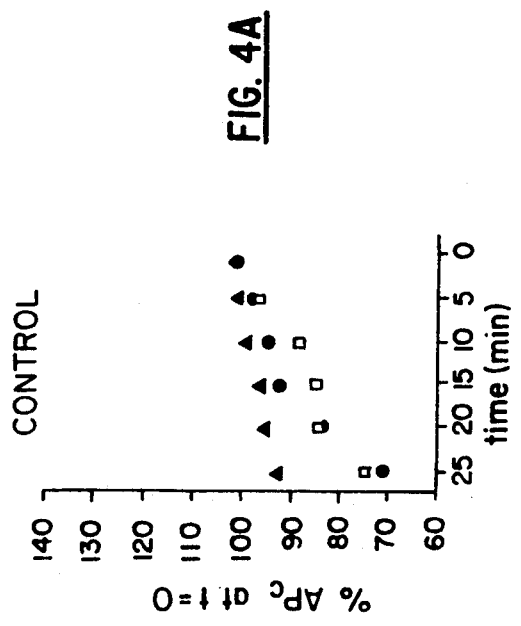
Figure 4E:
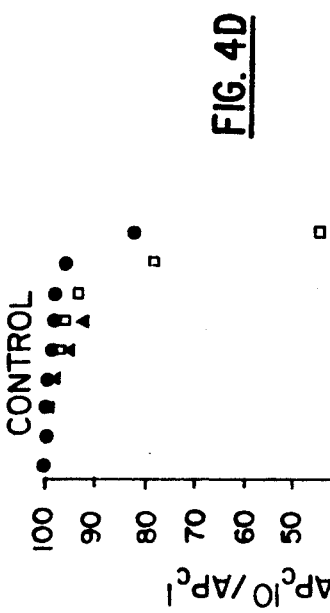
Figure 4C:
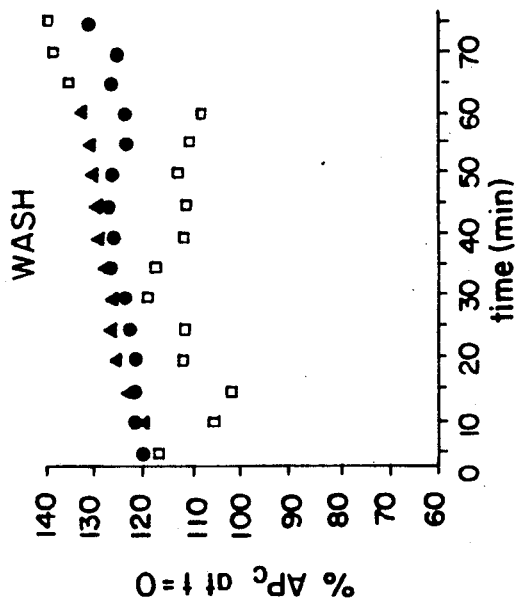
Figure 4F:
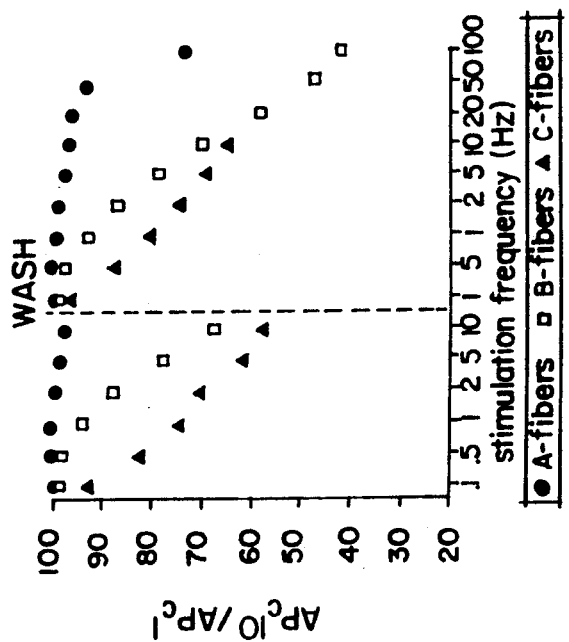

Nerves were desheathed and mounted in an acrylic sucrose-gap chamber (FIG. 2C). We used a method after that described by Stampfli [Stampfli, R., *Experientia* 10:508–509 (1954); see also Rando et al., *Mol. Pharmacol.* 29:467–477 (1986)]. One end of the nerve was stimulated by bipolar extracellular electrodes (silver/silver chloride) in small pools (approximately 50 μl each) containing control buffer solution and isolated from the recording pools by petroleum jelly. An 8-mm length of intact, desheathed nerve was exposed to drugs in the test pool (approximately 300 μl) containing one of the silver/silver chloride recording electrodes; the other electrode rested in a HL solution that bathed the other, "intracellular" cut end of the nerve. These two recording zones were separated by a sucrose gap consisting of a hollow cylinder of 3 mm diameter that intersected the nerve to perfuse it with the insulating, non-ionic sucrose (isotonic at 0.25M). Because of the removal of extracellular ions in the sucrose gap by continuous perfusion of the non-electrolyte (2–3 ml/min.), the $AP_c$ cannot propagate through this region. The potential between the two electrodes is proportional to the true transmembrane potentials, averaged for the different fibers. This measurement includes a direct current (DC) offset, which is representative of the average resting potential (the compound resting potential [CRP]), plus the true monophasic action potentials from the different fiber types. In contrast to the extracellular chamber described above, which measured $AP_c$ in a drug-free segment after they had propagated through a VTD solution, the sucrose gap measured the behavior of the nerve membrane directly exposed to drug, the "veratrinized" nerve.

$AP_c$ and the CRP were recorded with the same amplifier used for extracellular recording (see above), but passed both to the DC-coupled input of the storage oscilloscope (for $AP_c$) and to a strip-chart recorder (for CRP) (model 8376-20, Cole-Palmer). $AP_c$ were elicited by supramaximal pulses with the same stimulus parameters for exciting A-, B- and C-fibers as used for extracellular recording, described above.

RESULTS FOR EXAMPLES 1–3

The results reported here are means ±SEM; the numbers of independent observations are also included. A two-tailed Student's t test was used to evaluate the significance of changes produced by the drugs.

EXTRACELLULAR RECORDING

1. Single Stimuli

The standard protocol used for testing the action of VTD was to record the $AP_c$ elevations in control HL solution for 30–60 min. before adding VTD; for 60–75 min. during VTD application; and for 60–75 min. after replacement with VTD-free HL. Single stimuli and trains of ten stimuli, at intensities and durations sufficient to excite either almost all A-fibers alone, or all A- and B-fibers, or all A-, B- and C-fibers, were applied intermittently during these three periods.

Recordings of the separate elevations corresponding to these different fiber types in a desheathed nerve are shown in FIGS. 3A–C for A- and B-fibers and in FIGS. 3D–F for C-fibers in a nerve exposed to 2 μM VTD, the highest concentration we used on desheathed nerves. During the control period, the period of VTD exposure, and the washout period, the amplitude of the singly-stimulated $AP_c$ for A- and C-fibers increased continually. Some slowing and separation of the B-fiber elevation is evident in FIG. 3B, but this was an exceptional case, contrasting the average behavior, which is plotted in FIG. 4. The trend of increasing $AP_c$ is shown in the top panels of FIG. 4, which graphs the $AP_c$ elevations averaged from multiple nerves exposed to 0.5 μM VTD. Average amplitudes of single $AP_c$ elevations in four nerves during periods of control, VTD exposure, and wash are (relative to the amplitudes at the beginning of VTD exposure [see FIG. 5]): 92±1, 85±4 and 97±1% (control); 117±7, 105±23, and 111±5 (VTD); and 123±14, 108±31 and 133±15% (wash) for A-, B-, and C-fibers, respectively.

In Example 2, control experiments (in which no VTD was added) yielded action potential elevations, at times equivalent to those of VTD exposure for 35 min., of 118, 126, and 97% for A-, B-, and C-fibers, respectively (see Example 2: Control Recording). Comparison of these controls to the values for $AP_c$ after 60 min. in VTD shows no significant difference for A- and B-fibers (P>0.05) but a significant enhancement of the C-fiber component (P<0.005) from exposure to VTD. Altogether, the continuity of the $AP_c$ increase in all three exposure periods and the comparable values with control measurements show that VTD at 0.5 μM has only a small effect on impulses conducted in response to a single stimulus.

2. Repetitive Stimuli

During a train of action potentials resulting from repetitive stimulation, the different $AP_c$ elevations diminished in a characteristic VTD- and frequency-dependent manner. Examples of this behavior are shown in FIG. 5. At 2 μM VTD, the response of A-fibers during 100-Hz stimulation was almost identical to that in drug-free solutions before and after VTD exposure (FIGS. 5A-C). The elevations declined slightly (by about 15%) at the second stimulation but remained constant during the rest of the train. This effect was due to the normal refractory behavior of the A-fibers.

The B-fibers were more sensitive to VTD, and at 50-Hz stimulation frequency there was a decline (by 70%) in their $AP_c$, which exceeded the fiber component of the $AP_c$ was often difficult to resolve because of its nearness to the A-fiber peak and its usually smaller amplitude. Still, as illustrated in FIG. 5E, we often could discriminate two separate peaks of the B-fiber component during repetitive stimulation. The selective slowing of a subclass of B-fibers (or of some other more slowly conducting myelinated fibers in the vagus nerve) that causes this peak separation accounted for a large part of the reduction in the peak height of the $AP_c$. Here, the compound amplitude declined clearly as a result of conduction dispersion as well as of some extinction of impulses. Upon removal of VTD, the differential slowing was reversed, and in the single volleys the superposition was restored, sometimes leading to a B-fiber amplitude greater than that of the A-fibers. However, the use-dependent effects of VTD on 13-fibers were not abolished completely by 75 min. of washing with drug-free HL (FIG. 5F).

Repetitive stimulation of C-fibers at much lower frequencies produced a marked fall in the corresponding $AP_c$ C-fiber elevation (FIGS. 5G-I). During a train of $AP_c$ at 10 Hz in 0.2 μM VTD, the C-fiber elevation decreased incrementally with each stimulus and reached a steady state elevation of about 40% relative to the amplitude of the first elevation in the train. The same stimulus pattern produced a decline of only 12% before VTD, and after about 1 h of VTD wash-out, this inhibition recovered to 22%, approximately one third of the decline during VTD exposure. The peak separation evident in the B-fiber elevation was never seen in C-fibers.

The average use-dependent decline of impulses from the different fiber types are graphed in FIG. 4 (bottom) and are listed in Table 3. During the period of VTD exposure, corresponding to the experimental times indicated on the horizontal axes of the upper panels, trains of ten stimuli were applied, and the ratio of the amplitude of the last $AP_c$ to the first $AP_c$ was measured (e.g., see FIG. 5). Two cycles of these stimuli were applied during the 75 min. of VTD treatment, the first from 0.1 to 10 Hz and the second from 0.1 to 100 Hz for A- and 13-fibers but only to 10 Hz for C-fibers, ranges within their normal physiologic discharge frequencies. The selective depression of this use-dependent effect on C-fibers is evident in the comparison of the control and VTD entries of Table 3.

Washing the nerves with VTD-free HL did not reverse the use-dependent depression of A- or B-fibers, but effected a partial reversal in the case of the C-fibers (Table 3). In control nerves continuously exposed to HL for up to 60 min., the intrinsic use-dependent decline of $AP_c$ increased by no more than 10% of the control values. Use-dependent decline of $AP_c$ in VTD-free nerves recovered within 1 or 2 s of the termination of rapid stimulation in all fiber types (data not shown), unlike the VTD-induced use-dependent effects, which can take tens of seconds to recover. The endogenous use-dependent decline of $AP_c$ seems to involve mechanisms different from those that mediate the actions of VTD.

TABLE 3

Use-dependent Reduction of $AP_c$ by Veratridine

| Fiber Type | Experimental Period | | |
|---|---|---|---|
| | Control (Before) | VTD | HL (Wash) |
| A* | 18.0 ± 2.0 | 25.3 ± 3.5§ | 27.0 ± 2.8 |
| B | 23.0 ± 7.0 | 55.0 ± 2.8§ | 52.6 ± 3.7 |
| C | 7.0 ± 1.5 | 54.6 ± 3.8§ | 34.6 ± 3.8 |

Values are percent inhibition of the tenth $AP_c$ in a train compared to the first. Means ± SEM from four separate experiments. [VTD] = 0.5 μM for all fiber types.
*Measured at 100-Hz stimulation frequency 5 min. before VTD (control), after 75 min. in VTD (VTD), and after 75 min. of wash in VTD-free (HL).
Measured at 50-Hz stimulation frequency 10 min. before VTD (control), after 70 min. in VTD (VTD), and after 70 min. in VTD-free wash (HL).
Measured at 10-Hz stimulation frequency 12 min. before VTD (control), after 60 min. in VTD (VTD), and after 60 min. in VTD-free wash (HL).
§$p < 0.001$, VTD versus control values.

Another view of this use-dependent effect is provided in FIG. 6, where the C-fiber responses to sequential stimuli in a train are superimposed in one record. The $AP_c$ response to the second stimulus in the train not only was much smaller in amplitude than the first, but also was conducted more slowly (FIG. 6B). The peak of the second wave arrived at the recording electrode with about 20% longer latency than that of the first wave. Subsequent stimuli produced a more gradual diminution in amplitude and slowing of conduction in the C-fibers. In the absence of VTD, neither the diminution in amplitude nor the slowing of conduction occurred (FIG. 6A). When stimulation ceased, the $AP_c$ recovered the form it had taken before the train, although this recovery sometimes took as long as 1-2 min., depending on the VTD concentration (data not shown).

The use-dependent reduction in the separate elevations of the $AP_c$ was measured at three VTD concentrations and at several stimulation frequencies. The frequencies, chosen to fall in the range of normal responses to physiologic stimuli among the three fiber types, extended to 100 Hz for A- and B-fibers but only to 10 Hz for C-fibers. Averaged relative amplitudes at the end of a train are graphed in FIG. 7. Each fiber class is characterized by a surface topography. Any vertical plane perpendicular to the frequency axis (x axis) intersects the surface along a dose-response curve that characterizes that particular fiber type at that particular frequency. If the vertical plane is instead drawn perpendicular to the drug axis (y axis), then the surface intersect shows the frequency dependence of the inhibition for that VTD concentration.

Figure 7A:
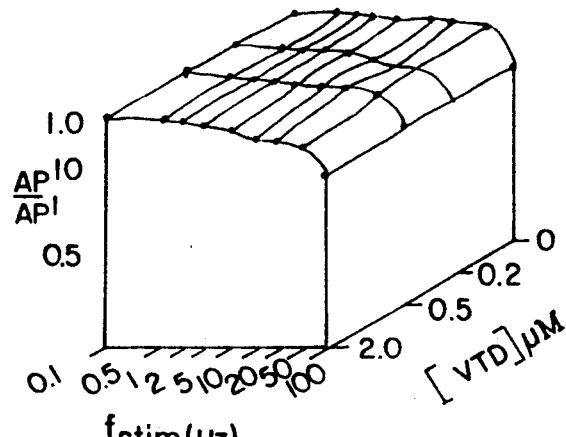
FIGS. 7A-C depict three-dimensional graphs of use-dependent VTD inhibition of compound action potentials of A-fibers (A), B-fibers (B), and C-fibers (C). The ratio of amplitudes of the tenth to the first $AP_c$ in a train of impulses, stimulated at 0.1-100 Hz for A- and B-fibers and at 01-10 Hz for A- and B-fibers and at 0.1-10 Hz for C-fibers, is plotted for VTD concentrations of 0-2.0 µM. The open circle is the amplitude of a single $AP_c$ in zero VTD. Broken lines fill the surface where there are no data points. Values are averages of four to five separate experiments.
Figure 7B:
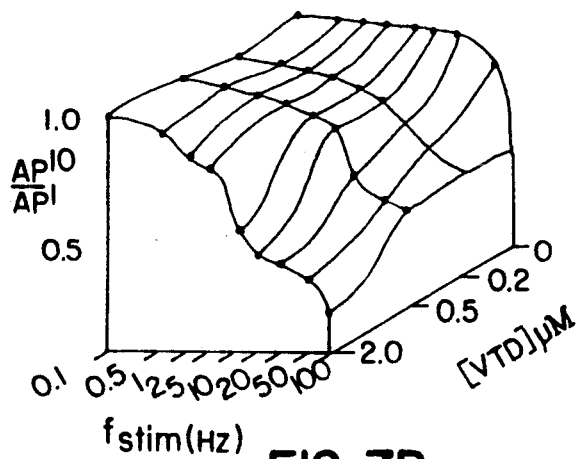
Figure 7C:
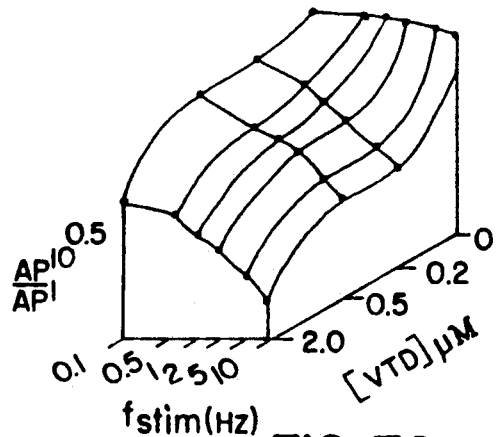

Examination of the parallel y-axis intersects in FIG. 7A shows that impulses in A-fibers are modified little by VTD up to 2 $\mu$M. B-fibers show more sensitivity to this drug (FIG. 7B), although we are less confident of these data since the B-fiber elevations were often small and superimposed on the "tail" of the A-fibers and bifurcated during the train (see above). The C-fiber elevations are diminished most by VTD, and at relatively low frequencies (FIG. 7C).

SUCROSE-GAP RECORDINGS IN THE VERTRINIZED REGION

Previous studies have reported that VTD has a depolarizing action on the membrane directly exposed to the drug. In order to observe this effect in the vagus preparation, we mounted desheathed nerves in a sucrose-gap chamber (see Conditions for Examples 1-3). This permitted the measurement of average monophasic action potentials and resting potentials from the 8-mm length of nerve bathed by the drug.

Control $AP_c$ measurements before VTD addition declined continuously but slowly with time, because in the sucrose-gap chamber the electrical activity is less stable than in the extracellular chamber. However, the CRP was steady. As shown by FIG. 8, after the addition of VTD (0.5 $\mu$m), the A-and B-fiber elevations remained unchanged. The C-fiber elevation also was unaffected for a single stimulus, but a slowly rising, VTD-induced depolarization (VID) developed within about 100 ms of stimulation (FIG. 8C) and decayed only slowly: the decay halftime was 3-4 s after 1 hr in 2.0 $\mu$m VTD (FIG. 8D). At high enough stimulation frequencies, the VID and the primary C-fiber response overlapped. Because of their very slow decay, the VIDs accumulated to yield a larger sustained depolarization (FIG. 9B), and the primary C-fiber elevations that were superimposed on this integrated depolarization were much smaller than were the elevations induced by single stimuli (FIGS. 9C and D). The VID occurred only when the stimulus conditions were sufficient to excite C-fibers, and the elevations of A- and B-fibers superimposed on the VID were approximately the same amplitude as those from stimulation of A-and and B-fibers alone. Therefore, the VID observed at these frequencies and VTD concentrations depended on activation of impulses in C-fibers, and correspondingly, affected impulses in those fibers only.

EXAMPLE 4

Recordings from Sheathed Nerves

We tested the ability of VTD to penetrate the tissues ensheathing the vagus nerve. Nerves with intact sheaths were arranged in the same extracellular recording chamber as had been used for the desheathed nerve studies just described. Because of the electrical isolating qualities of the sheath, stimulus requirements are greater and the recorded $AP_{C}s$ are smaller, but have the same latency from stimulation as in the desheathed nerves. These $AP_{C}s$ also were inhibited selectively by VTD. However, the onset of the effect was much slower and the VTD dose requirement much higher: 2 $\mu$M VTD took approximately 30 min. to affect the C-fibers detectably, and 10 $\mu$M took approximately 15 min. (compared to the time-course shown in FIG. 4). This is expected in a lipophilic base for which more than 90%, on average, of the drug molecules are ionized [Kupchan and By, "The Veratrum Group," in Alkaloids, Vol. 10, Manske, R.H.F. (ed.), New York, Academic Press (1968), pp. 193-285].

Nevertheless, the same phenomenon that had been observed in desheathed nerves occurred: the C-fiber elevation was progressively inhibited in a use-dependent fashion. The use-dependent reduction at 10 Hz after a 60-min. exposure of an desheathed nerve to 10 $\mu$m VTD was only approximately 30% of that achieved at steady state on a desheathed nerve by 0.2 $\mu$m VTD. Therefore, if the sheath does not modify the drug's action but only slows its access, the rate of penetration into the nerve is reduced at least 50-fold by the sheath.

The action of VTD increased throughout the exposure period (75 min.) and persisted or even grew during the subsequent washout. In both nerves tested, a steady-state effect, reached during the wash-out period, remained constant for up to 3 h in drug-free solution.

EXAMPLE 5

Sensory and Motor Block of Rat Sciatic Nerve In Vivo Produced by the $Na^+$ Channel Activator Veratridine The in vivo local anesthetic activity of VTD was assayed.

Male Sprague-Dawley rats (200-250 g) were divided into 4 groups of 10 each. 0.1 ml of VTD alone at 0.2, 0.5 or 0.7 mM or vehicle (saline) was injected at the depression between the femoral head and the hip. The same animals were injected with VTD with epinephrine (EPI, 1:200,000) one week later, using the previously uninjected leg. Motor and sensory functions were rated by the respective monitoring of toe curling and/or foot dragging, and by testing the nocifensive withdrawal reflex to pinch of the foot pad of the injected hindlimb. Saline alone affected neither function.

TABLE 4

| | I. VTD Alone | | | |
|---|---|---|---|---|
| [VTD] (mM) | fraction block | onset (min.)* | duration (min.)* | fraction salivating |
| MOTOR | | | | |
| 0.2 | 8/10 | 13 ± 2 | 124 ± 19 | 0/10 |
| 0.5 | 10/10 | 10 ± 3 | 211 ± 31 | 4/10 |
| 0.7 | 5/10 | 6 ± 2 | 285 ± 39 | 10/10 |
| SENSORY | | | | |
| 0.2 | 1/10 | 13 | 51 | |
| 0.5 | 2/10 | 3 ± 1 | 224 ± 44 | |
| 0.7 | 4/10 | 10 ± 2 | 115 ± 1 | |

(*$\bar{x}$ ± SEM)

As shown by Table 4, VTD alone produced motor block in 6-12 min. lasting for approximately 100-300 min. Sensory block occurred less frequently. Toxic signs, including profuse salivation, were observed in 14/20 of rats receiving 0.5 and 0.7 mM VTD alone. As shown by Table 5, the co-injection of VTD with EPI increased the fraction of successful blocks, did not significantly alter onset or duration times, but dramatically reduced toxicity.

TABLE 5

| | II. VTD + EPI | | | |
|---|---|---|---|---|
| [VTD] (mM) | fraction block | onset (min.)* | duration (min.)* | fraction salivating |
| MOTOR | | | | |

TABLE 5-continued

| | II. VTD + EPI | | | |
|---|---|---|---|---|
| [VTD] (mM) | fraction block | onset (min.)* | duration (min.)* | fraction salivating |
| 0.2 | 9/10 | 21 ± 5 | 143 ± 19 | 0/10 |
| 0.5 | 10/10 | 12 ± 3 | 225 ± 15 | 0/10 |
| 0.7 | 10/10 | 9 ± 3 | 265 ± 18 | 1/10 |
| | | SENSORY | | |
| 0.2 | 3/10 | 19 ± 3 | 20 ± 6 | |
| 0.5 | 5/10 | 34 ± 10 | 82 ± 27 | |
| 0.7 | 5/10 | 25 ± 14 | 123 ± 27 | |

(*x̄ ± SEM)

EXAMPLE 6

For comparison, the local anesthetic bupivacaine (0.75%=23 mM) produced motor blockade in 86% (205/239) of rats tested: onset=4.8 min., duration=161 min. Similarly, lidocaine (2%=74 mM) caused motor blockade in 96% (216/224) of rats; onset=1.9 min., duration=75 min., and sensory blockade in 100% (5/5) of rats; onset=1.3 min., duration=78 min.

We conclude that VTD is a more potent and longer acting inhibitor of motor function than either bupivacaine or lidocaine although nocifensive reflexes are blocked less predictably.

What is claimed is:

1. A method for inhibiting nerve impulses in an animal or human in need thereof comprising administering a therapeutically effective amount of veratridine or a pharmaceutically acceptable salt thereof, proximal to at least one C-fiber containing nerve.

2. A method for inhibiting nerve impulses comprising administering to an animal in need of such treatment and proximal to said C-fiber containing nerve an effective amount of a compound having the formula:

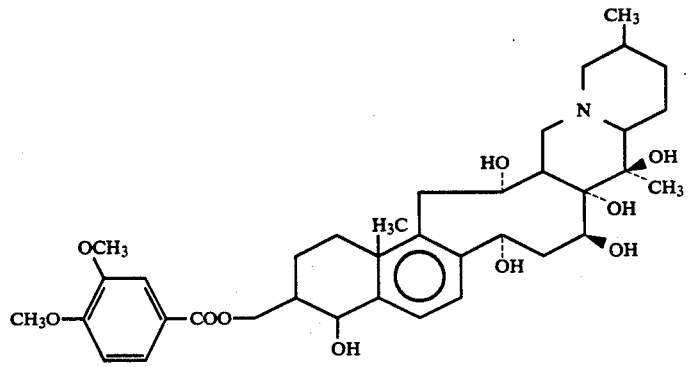

or a pharmaceutically acceptable salt thereof.

3. The method of claim 1 or 2 wherein said nerve comprises A-fibers, B-fibers, and C-fibers.

4. The method for inhibiting nerve impulses of claims 1 or 2 wherein said veratridine is co-administered with an amount of epinephrine effective to reduce toxicity in said animal or human.

5. A composition of matter comprising a therapeutically effective amount of veratridine or a pharmaceutically acceptable salt thereof in combination with an amount of epinephrine effective to mitigate the toxic side effects of veratridine.

6. The method of claim 1 or 2, wherein the compound veratridine or a pharmaceutically acceptable salt thereof is administered to said animal or human in an amount of from about 0.027 mg/kg of body weight to about 0.63 mg/kg of body weight.

* * * * *